United States Patent [19]

Connors et al.

[11] Patent Number: 5,726,009
[45] Date of Patent: Mar. 10, 1998

[54] NATIVE-STATE METHOD AND SYSTEM FOR DETERMINING VIABILITY AND PROLIFERATIVE CAPACITY OF TISSUES IN VITRO

[75] Inventors: Kenneth M. Connors; Anna Monosov, both of San Diego, Calif.

[73] Assignee: Anticancer, Inc., San Diego, Calif.

[21] Appl. No.: 578,663

[22] PCT Filed: Jun. 29, 1994

[86] PCT No.: PCT/US94/07476

§ 371 Date: Jun. 4, 1996

§ 102(e) Date: Jun. 4, 1996

[87] PCT Pub. No.: WO95/01455

PCT Pub. Date: Jan. 12, 1995

Related U.S. Application Data

[63] Continuation-in-part of Ser. No. 84,402, Jun. 29, 1993, abandoned, which is a continuation-in-part of Ser. No. 965,602, Oct. 22, 1992, abandoned, which is a continuation of Ser. No. 326,286, Mar. 20, 1989, abandoned.

[51] Int. Cl.$^6$ .................... C12Q 1/68; G01N 33/53
[52] U.S. Cl. ................... 435/4; 435/6; 435/69.1; 435/810; 436/501; 436/63; 514/2; 514/44; 935/77; 935/78
[58] Field of Search .................... 435/6, 69.1, 91.1, 435/4, 810; 436/501, 63; 536/23.1, 24.1, 24.3, 33; 935/77, 78; 514/2, 44

[56] References Cited

U.S. PATENT DOCUMENTS 4,060,081  11/1977  Yannas et al. ............ 128/156

FOREIGN PATENT DOCUMENTS

WO 90/11371  10/1990  WIPO.

OTHER PUBLICATIONS

Vescio et al. (1987) Proc. Natl Acad Sci (USA), vol. 84, pp. 5029–5033.
Samb et al. (1987) J. of Biol. Chem., vol. 262, No. 17, pp. 8390–8394.
Frankfurt et al., Cytometry, vol. 5, pp. 71–80 (1984).
Freeman et al., Proc. Natl. Acad. Sci. USA, vol. 83, pp. 2694–2698 (1986).
Leighton, J. Natl. Cancer Inst., vol. 12, pp. 545–561 (1951).
Ljung et al., Proc. Am. Assoc. Cancer Res., vol. 28, p. 34 (1987).
McDivitt et al., Cancer, vol. 57, pp. 269–276 (1986).
McGurrin et al., Cancer, vol. 59, pp. 1744–1750 (1987).
Meyer et al., Breast Cancer Rest. Treat., vol. 4, pp. 79–88 (1984).
Meyer et al., Cancer, vol. 51, pp. 1879–1886 (1983).
Slocum et al., Cancer Research, vol. 41, pp. 1428–1434 (1981).
Smith et al., Proc. Natl. Acad. Sci. USA, vo. 82, pp. 1805–1809 (1985).

*Primary Examiner*—Ardin H. Marschel
*Attorney, Agent, or Firm*—Morrison & Foerster

[57] ABSTRACT

The present invention relates to a method of using an in vitro culture system to measure the cellular proliferative capacity cellular viability of human tissues, particularlytumor tissues. The invention also describes the use of the method to evaluate the effectiveness of an antineoplastic drug in inhibiting tumor cell proliferation of viability.

16 Claims, No Drawings

NATIVE-STATE METHOD AND SYSTEM FOR DETERMINING VIABILITY AND PROLIFERATIVE CAPACITY OF TISSUES IN VITRO

This application is the national phase under 35 U.S.C. §371 of PCT application WO 95/01455, filed Jun. 29, 1994, which claims priority from U.S. application Ser. No. 08/084,402 filed 29 Jun. 1993 and now abandoned. This application is a continuation-in-part of U.S. Ser. No. 08/084,402, filed Jun. 29, 1993, now abandoned, which is a continuation-in-part of U.S. Ser. No. 07/965,602, filed Oct. 22, 1992, now abandoned, which is a file wrapper continuation of U.S. Ser. No. 07/326,286, filed Mar. 20, 1989.

DESCRIPTION

1. Technical Field

The present invention relates to a method of using an in vitro culture system to measure the cell proliferation and cell viability of human tissues, particularly tumor tissues, and thereby to measure the efficacy of anti-neoplastic drugs upon the proliferation and viability of the cultured cells.

2. Background

Cancer is a disease involving inappropriate cell division. A realistic model is greatly needed to understand the biology of altered proliferation in cancer as compared to normal tissue and to use information on proliferation capacity as a basis of cancer prognosis and treatment.

Measurements of proliferation capacity of tumors currently are obtained by thymidine-labeling index (TLI), by flow cytometric measurements of cells presumed to be in S phase, or by measuring a nuclear antigen, Ki-67, found in at least certain proliferating cell types. Meyer et al., *Breast Cancer Rest. Treat.*, 4: 79–88 (1984); McDivitt et al., *Cancer*, 57: 269–76 (1986); and McGurrin et al., *Cancer*, 59: 1744–50 (1987). Whichever method is used, the results obtained show that the higher the S-phase fraction is, the poorer the prognosis. Clinical studies utilizing the TLI procedure have been successful in identifying and determining therapy of a subgroup of lymph node-negative women with breast cancer having a 48% relapse rate. Meyer et al., *Cancer*, 51: 1879–86 (1983). There is therefore great potential value for cancer prognosis, therapy, and biology in determining the proliferative capacity of tumors.

However, As important as the measurement of the TLI seems to be, current methods of measuring the TLI are impractical and are not physiological. For breast tumors, assays must be conducted within approximately 2 hours of surgery, precluding a central laboratory from carrying out the measurement. Generally, the TLI is measured under very high atmospheric pressure in a salt solution to allow penetration of $^3$H-thymidine into the tissue. Under these conditions the tumor loses viability after a few hours and in many cases it must be assumed that cells capable of cycling are not measured since the time of measurement is so much less than the generation time of the asynchronous cells within the tumor. With regard to other human tumor types, there is very little information regarding measurement of proliferation capacity of surgical specimens.

While flow cytometry provides a more rapid method of measuring cell cycle kinetics and cells can also be assessed for aneuploidy, it presents the following technical problems: (i) Dissociation, either mechanically or enzymatically, into a single-cell suspension is required, resulting in loss of ability to observe tissue architecture and the potential selective loss of one or more specific populations of cells. Full evaluation of all the heterogeneous cell types of an individual tumor, including their spatial organization, is of obvious importance in the development of prognostic tests. (ii) Flow cytometry does not unambiguously distinguish between S-phase diploid cells and aneuploid resting or nonviable cells. This becomes an important issue, as studies have demonstrated that tumor cell subpopulations that are enriched in aneuploid cells are largely nonviable by dye-exclusion analysis. Frankfurt et al., *Cytometry*, 5: 71–80 (1984); Slocum et al., *Cancer Res.*, 41: 1428–34 (1981); and Ljung et al., *Proc. Am. Assoc. Cancer Res.*, 28: 34 (1987). (iii) In addition, the S-phase factions of diploid tumors are likely to be underestimated by flow cytometry due to contamination with non-proliferating, nonneoplastic cells. The invasive capacity of diploid cells in vitro from primary breast carcinomas has been clearly demonstrated. Smith et al., *Proc. Natl. Acad. Sci. USA*, 82: 1805–9 (1985).

The nuclear antigen Ki-67 seems to be present in proliferating breast cancer cells [McGurrin et al., *Cancer*, 59: 1744–50 (1987)], but its relevance to other tissue types is not yet known.

Perhaps most importantly, these techniques measure cells in S phase at a single point in time (flow cytometry, Ki-67) or after a very short labeling time (TLI). Thus, these measurements preclude an estimation of the total cell growth fraction of the tumor which may well reflect a more accurate measurement of the proliferative capacity of the tumor.

Importantly, none of the above methods have been applied to systematically measure the proliferation capacity of normal tissues, in particular in comparison with adjacent tumor tissues, nor have the above methods been applied systematically in comparative measurements of normal or tumor tissue proliferation in the presence of anti-proliferative or other therapeutic agents.

The determination of effective cytotoxic endpoints for chemotherapy is particularly important when one considers the heterogeneity of cell types in a tumor tissue and the possible difference between proliferating cells and those cells which a not proliferating but are viable in the tumor. Although a cytotoxic agent may exhibit effectiveness against proliferating cells in an in vitro assay, it must also be shown to be effective against non-dividing but viable cells in the tumor in order to be assured that all cells of the tumor are killed.

Furthermore, for accurate measurements of cytotoxic endpoints for effective use of cytotoxic agents, the use of prior in vitro assays which disaggregrate tumor cells does not provide a reliable test environment reflective of the three-dimensional architecture of the tumor tissue. Assays using disaggregated tissue provide equal and ready access of the cytotoxic agent to the cells of the tumor, which is not typical of in vivo tumor tissues.

The use of an in vitro chemosensitivity test system must provide results that can be readily measured and that reliably predict in vivo effectiveness of the cytotoxic agent being tested.

BRIEF SUMMARY OF THE INVENTION

The present invention provides in improved in vitro assay system to determine chemosensitivity of a preselected cell population in a normal or tumor tissue to a cytotoxic agent. In particular, the invention provides an improved system for measuring chemosensitivity of a tissue to a cytotoxic agent by measuring both the cellular proliferation and cellular viability of the cells from patient tissue biopsies when assayed in a native histocultured state.

Therefore, a method for measuring the tumor specific effects of an agent on cell proliferation and/or viability is also contemplated. The method comprises histoculturing, in separate containers, first and second portions of tumor tissue samples. The histocultured samples are exposed to one or more concentration of an agent whose effects are being examined. The two exposed samples are then treated (contacted) with either a proliferation marker or a cell viability marker, and the two samples are then further histocultured for a predetermined period of time. The percent of cells exhibiting proliferation and the percent of cells exhibiting viability in the histocultured samples is then determined, and, by comparing the results obtained from the treated tumor cells with results obtained from control untreated tumor cells, the tumor specific effect of the agent on cell viability and/or proliferation is determined.

In preferred embodiments, a normal tissue from a tissue analogous to the stem cells of the tumor is also histocultured to obtain further cytotoxicity data for the drug being tested.

It has also been found that the determinations as to cellular proliferation and viability made according to the present invention accurately predicts the grade, stage and overall aggressiveness of a tumor.

DETAILED DESCRIPTION OF THE INVENTION

The present invention provides a method for measuring the effectiveness of an agent as an chemotherapeutic agent on normal or tumor cells in their native environment, i.e., as part of a tissue. In carrying out such "drug" sensitivity measurements, the effect on the viability and proliferation of cells of the tissue to exposure to one or more given dose levels of one or more given drugs is measured by individually culturing aliquots of the same explanted tissue using a plurality of containers, and determining the drug's effect on both proliferation and viability of cells in the tissue. One of the aliquots serves as a control and is quantitatively assayed for cell viability and/or proliferation in the absence of drug exposure. Each of the other aliquots is exposed to the drug at a different dose level and then quantitatively assayed for viability and/or proliferation by the methods described herein.

A. Histoculture Methods

Any suitable method may be used for culturing the tissue, so long as the three dimensional architecture of the tissue to be evaluated is maintained. Culturing of intact tissue to preserve the three dimensional architecture is referred to herein as histoculture. Maintenance of tissue architecture is important to accurately reflect the in vivo growth characteristics of the tissue, and in the case of a tumor tissue to reflect the potential in vivo responsiveness of the tumor to a test agent. Typical histoculturing methods include those described by Freeman et al., Proc. Natl. Acad. Sci. USA, 83: 2694–2698, 1986; and Vescio et al., Proc. Natl. Acad. Sci. USA, 84: 5029–5033, 1987 (these references, and others cited herein, are hereby incorporated by reference in this application).

Normal or tumor specimens are typically explanted for histoculture by an aseptic surgical procedure and minced aseptically into about 0.5 to 1.0 mm³ pieces. Best results are obtained with approximately cubical 1 mm³ pieces. Preferably, multiple portions of a tissue are examined in parallel culture assays because of the heterogeneous nature of most tissues, particularly tumors. As discussed herein, the method of this invention permits the heterogeneity of the tissue to be taken into account.

In order to more effectively produce tumor fragments of suitable size for histoculture, a multiblade scalpel can be used consisting of 2 to 100 scalpel blades mounted in parallel on the end of a handle, with spaces of 1 mm (for example) between blades. This multi-blade format allows for more rapid, accurate and reproducible cutting of cubes of tissue 1 mm on a side.

The tissue pieces to be cultured are placed on a suitable support material in one or more separate containers or wells. The support material may be any suitable material having a trabecular structure with interstices capable of delivering aqueous nutrients from a liquid medium in contact with the support by capillary action to the tissue pieces. The support material may be a suitable mesh formed from a synthetic resin such as nylon, borosilicate glass fiber, polypropylene or a natural organic material such as cellulose or collagen. In addition, the support material can be coated with, or covalently linked to, extracellular matrix materials such as fibronectin or laminin. For example, fibronectin binds to collagen through strong non-covalent interactions, and laminin can be linked to gelatinized pig skin using crosslinking agents such as dimethyl suberimidate. Preferably, human fibronectin or human laminin are used for human tissues, allowing a more accurate model of the extracellular interactions occurring between a tumor and extracellular matrix in human beings.

Preferred materials include gelatinized pig skin, described by U.S. Pat. No. 4,060,081 to Yannas et al., a collagen-containing gel available from Health Designs, Inc. (Rochester, N.Y.) or the Upjohn Company (Kalamazoo, Mich.) under the Gelfoam trademark, a homopolysaccharide sponge of the sort described by Leighton, J. Natl. Cancer Inst. 12: 545–561 (1951) and combinations of collagen-containing gels and homopolysaccharide sponge materials.

Various liquid tissue culture nutrient media capable of supporting tissue cell growth are known in the art. The medium used can either be serum-containing or serum-free with additives such as insulin, transferrin, selenium, estradiol and the like. A culture medium found to be particularly suitable in the present invention is Eagle's minimal essential medium (MEM) [Eagle, Science, 122: 501 (1955) and Eagle, Science, 130: 432 (1959)].

The tissues are typically histocultured for at least 1–5 days prior to exposing the cells therein to the agent being examined. Culturing is typically performed in a humidified atmosphere at a temperature corresponding to that of the body temperature of the animal from which the tissue sample came, e.g. 37 degrees C for human tissue samples. Exemplary histoculture conditions are described in the Examples.

B. Cell proliferation Assays

According to the present invention, the histocultured tissue is assessed for chemosensitivity to a candidate agent by measuring the proliferative capacity of cells in the tissue upon and/or after exposure to the agent. Proliferation (i.e., multiplication) of the cells occurs by cell division and therefore may be measured using a variety of proliferation markers sensitive to cell division. Furthermore, different types of cells in the intact tissue may exhibit different degrees of proliferation upon or after exposure to the agent, providing further information about the tissue, and in cases of a tumor tissue, about the stage, grade and/or aggressiveness of the tumor.

A typical measure of cell proliferation involves the incorporation of a DNA-synthesis marker into the proliferating cells. That is, the number of proliferating cells in the tissue is indicated by the number of cells in the histocultured tissue sample having metabolically incorporated the DNA-synthesis marker into the cellular DNA during cell division associated with cell proliferation.

Proliferation markers for cellular DNA-synthesis are also well known in the art and include radioactively labeled nucleotides such as $^3$H-thymidine, $^3$H-deoxyadenosine, $^3$H-deoxyguanosine, $^3$H-deoxycytidine, 3-deoxyuridine and the like.

Exemplary conditions for incorporation of DNA-synthesis markers to measure cell proliferation, and the analytical methods for assessing proliferation, are described in the Examples.

The assessment of proliferation capacity can be expressed as "growth fraction index" (GFI) of a tissue. In preferred embodiments, the growth fraction index of a tumor tissue correlates to the tumor's in vivo grade and stage, i.e., the in vivo aggressiveness of the tumor, particularly in breast and ovarian carcinomas.

The growth fraction index is determined by histoculturing, as described herein, a sample of cells in an intact tissue. The cells are then treated with a proliferation marker such as one of the before-described DNA-synthesis marker, e.g., $^3$H-thymidine. The treated cells are cultured for a predetermined period of time and then the percent of sample cells containing the proliferation marker incorporated into the cellular DNA is determined, that percentage representing the tissue's intrinsic growth fraction index.

The GFI for a particular tissue is the percent of proliferating cells in a population of total cells in the treated histoculture. GFI is expressed as a percent and is calculated as the number of proliferating cells (P) divided by the number of total cells (T) times 100. The formula for GFI can be expressed as GFI=100×P/T. The GFI value is typically calculated independently for duplicate samples, one a control and the other treated with the agent, after similar culture conditions and times. A reduction in GFI of 50% or greater for the treated cultures compared to control was indicative of in vitro sensitivity to the drug.

C. Cell Viability Assays

According to the present invention, the histocultured tissue can also be assessed for chemosensitivity to a candidate cytotoxic agent by measuring the viability of cells in the tissue upon and/or after exposure to the agent. Viability of the cells may be measured using a variety of viability markers. Furthermore, different types of cells in the intact tissue may exhibit different degrees of viability upon or after exposure to the agent, providing further information about the chemosensitivity of individual cell types within the tissue.

A typical measure of cell viability involves detecting cellular metabolism in the cell, such as by using metabolic markers indicative of viability. Such markers of cell viability are well known and include assays of cell membrane integrity (viable dye exclusion or incorporation), protein synthesis (uptake of labeled amino acids into newly synthesized protein), and other metabolic markers. The number of viable cells in each tissue sample is indicated by the number of cells that incorporate a metabolic marker or that otherwise exhibit viability.

i. Protein Synthesis Markers

In one embodiment, the incorporation of a label into a cellular protein during protein synthesis (i.e., a protein-synthesis marker) is indicative of cell viability insofar as cellular metabolic activity is occurring upon incorporation of the marker. Metabolic markers for cellular protein synthesis are well known in the art and include radioactively labeled amino acids such as $^{35}$S-methionine, $^{14}$C-alanine, $^{14}$C-glycine, $^{14}$C-glutamic acid, $^{14}$C-proline, $^3$H-leucine, $^3$H-serine and the like. Exemplary protein synthesis markers are used as described in the Examples for measuring viable cells in a histocultured tumor tissue sample.

ii. Viability-Specific Dyes

In another embodiment, dye exclusion or dye incorporation can be utilized to indicate the presence of viable cells in a tissue sample. For example, cells which incorporate a dye specific for dead cells are scored non-viable, and cells which exclude the dead cell-specific dye are scored as viable. Conversely, dyes specific for viable cells can be used to directly on the histoculture to indicate the presence of viable cells.

As used herein, the phrase "specific for dead cells" means that the indicator is taken up or incorporated only into dead, non-viable cells.

Typically, dyes specific for dead cells are compounds with a high ionic charge and low permeability such that the dyes cannot permeate intact cellular membranes. When cells die, the membrane is structurally or functionally ruptured such that dyes specific for dead cells gain access to the intracellular space where they bind to intracellular components such as nuclear membranes.

A preferred dead cell-specific indicator is a dye capable of optical detection. See, e.g., Handbook of Fluorescent Probes and Research Chemicals, ed. by R. P. Haugland, Molecular Probes, publisher, Eugene, Oreg. (1989–1991). A preferred dead cell-specific dye is a fluorescent dye such as propidium iodide (PI), ethidium bromide (EtBr), ethidium homodimer [(5,5'-diazadecamethylene) bis (3,8-diamino-6-phenyl-phenanthridium) dichloride, dihydrochloride] and the like. Most preferred is propidium iodide for use as a dye specific for dead cells. Propidium iodide and other dyes specific for dead cells are well known in the art and are commercially available (Molecular Probes, Eugene, Oreg.).

iii. Metabolism Markers

In another embodiment, cell viability can be measured by detecting the consumption of a metabolite from the histoculture medium. A typical consumption endpoint metabolite is glucose.

In a related embodiment, cell viability can be measured by the use of a metabolic substrate which is converted into a detectable product upon reaction with a cellular component indicative of cell viability. An exemplary metabolic substrate is any of the tetrazolium salts which are converted by the action of cellular dehydrogenases into a detectable formazan compound.

A suitable tetrazolium salt solution is prepared by dissolving the selected salt in a suitable stock solution such as saline, which is preferably phosphate-buffered. Typical tetrazolium salts include 3-[4,5-dimethylthiazol-2-yl]-2,5-diphenyltetrazolium bromide (MTT), 2,2',5,5'-tetra-p-nitrophenyl-3,3'-[3,3'-dimethoxy-4,4'-diphenylene] ditetrazolium chloride (TNBT), 3,3'-[3,3'-dimethoxy(1,1'-bi-phenyl)-4,4'-diyl]-bis[2,5-diphenyl-2H-tetrazolium] dichloride (tetrazolium blue; TB), 2,3,5-triphenyltetrazolium chloride (tetrazolium red; TR), 2,5-tiphenyl-3-[α-naphthyl]-tetrazolium chloride (tetrazolium violet; TV), 2-[4-iodophenyl]-3-[4-nitrophenyl]-5-phenyltetrazolium chloride (INT), 2,2',5,5'-tetraphenyl-3,3'-[p-diphenylene]ditetrazolium chloride, 2,2'-di-p-nitrophenyl-5,5'-diphenyl-3,3'-[3,3'-dimethoxy-4,4'-diphenylene]ditretrazolium chloride (NBT), 2,2'-di[p-nitrophenyl]-5,5'-di[p-thiocarbamylphenyl]-3,3'-[3,3'-dimethoxy-4,4'-biphenylene]ditretrazolium chloride (TC-NBT), and mixtures thereof.

The selected tetrazolium salt, preferably MTT, is dissolved in a suitable medium, typically phosphate-buffered saline (PBS). The preferred concentration is from about 4 mg/ml to 12 mg/ml, with optimum results at about 8 mg/ml. The solution is preferably filtered before use. From about 50 to 150 µl of the MTT solution is added to each tissue sample. Best results are obtained with about 100 µl. The samples are preferably again incubated for about 1 to 3 hours under incubation conditions as described herein.

The samples are then removed, frozen, and frozen sections of about 4µ are made in a conventional manner. The resulting slides are then dipped in a suitable fluorescent dye solution for from about 30 seconds to 2 minutes to allow the stain to penetrate the section and stain all the cells in the section, providing a detectable indication of the total number of cells in the section, dead or alive. A 1 minute dip is preferred. Typical suitable stains for labelling cells are any stain that is specific for cells and which is detectable by light microscopy. Preferred are the family of fluorescent dyes that intercalate DNA and thereby fluoresce, indicating the presence of nuclei. Such dyes are generally known as high-affinity nucleic acid stains. Exemplary fluorescent dyes are ethidium bromide (EtBr), ethidium homodimer, propidium iodide (PI), and the like dyes available from Molecular Probes, Inc., (Eugene, Oreg.). Particularly preferred is PI, and is utilized as exemplary herein. In each case where a different stain is used, a filter system is selected to produce light of wavelengths to which the fluorescent dye is sensitive.

The slides are then dried and examined with a microscope, typically at about 200 X utilizing a video camera attached to the microscope. The sections are first illuminated with polarized light, typically generated by a mercury lamp. The cells containing formazan crystals due to metabolically reduced tetrazolium salt brightly reflect polarized light. The images are analyzed by pixel image analysis, typically as described by Hoffman et al, *Proc. Natl. Acad. Sci. USA*, 86: 2013–2017, (1989).

The slides are also analyzed for fluorescence using light passed through a filter providing the proper wavelength to activate the selected fluorescent dye. The number of bright pixels from the fluorescence or reflectance measurement is calculated using a modified Fas-Com version of the P-See program from The Microworks, Del Mar, Calif., typically run on an IBM PC XT type computer. Cell morphology can be observed due to the fluorescence whereby cancer cells can be distinguished from stromal cells. The slide images are digitized by a conventional digitizer board and the area of brightness corresponding to the number of labeled or bright cells is calculated as the area of enhanced pixels by the Fas-Com program. The area of enhanced pixels is proportional to the number of labeled cells and may represent the number of viable cells when labeled with a viability marker such as MTT, and represents the total number of cells when labeled with a total cell specific dye. The ratio of formazan bright pixels to fluorescent dye bright pixels can be calculated for each drug tested and compared to a control value to obtain the amount of drug-induced inhibition.

For example, the sensitivity of a tumor tissue to a cytotoxic drug expressed as viable cell inhibition rate can be determined by using the formula:

$$\text{Inhibition rate} = \frac{100 - [(PIAFC_{Treated}/PIAFD_{Treated})/(PIAFC_{Control}/PIAFD_{Control}) \times 100]}{}$$

where PIAFC is pixel image analysis of formazan crystal reflection and PIAFD is pixel image analysis of fluorescent dye emissions.

Using a viability marker as described above, one can also determine the viable cell index (VCI) of the cells in the tissue following exposure to a chemotherapeutic agent of interest, when compared to untreated control tissue culture. VCI is a measure of the percent of viable cells in a population of total cells in the treated histoculture. VCI is expressed as a percent and is calculated as the number of viable cells (V) divided by the number of total cells (T) times 100, where T is viable cells (V) plus dead cells (D). The formula for VCI can be expressed as $VCI=100 \times V/(V+D)$. The VCI value can be calculated for duplicate samples, one a control and the other treated with the agent, after similar culture conditions and times. A reduction in VCI of 50% or greater for the treated cultures compared to control was indicative of in vitro sensitivity to the drug.

Typically, the number of dead cells (D) is measured by counting cells labeled with a dye specific for dead cells, as described herein. Similarly, the number of viable cells is measured by counting cells labeled with a dye or metabolic marker specific for viable cells. As used herein, the phrase "specific for viable cells" means that the indicator/marker is taken up (incorporated) or detectable in living, but not dead, cells.

The indicator specific for viable cells may be a metabolic precursor or a non-metabolite that gains access to living cells.

A preferred non-metabolite indicator specific for viable cells is a dye that is capable of optical detection. Any dye recognized in the art as being specific for viable cells can be used in accordance with the toxicity assay of this invention. See, e.g., Handbook of Fluorescent Probes and Research Chemicals, ed. by R. P. Haugland, Molecular Probes, publisher, Eugene, Oreg. (1989–1991).

In a preferred embodiment, the dye is a fluorescent dye. Exemplary viable cell-specific fluorescent dyes are BCECF-AM [B-1150: 2'7'-bis-(2-carboxyethyl)-5-(and-6)-carboxyfluorescein acetoxymethyl ester], calcein-AM (C-1430: glycine-N,N'-((3',6'-dihydroxy-3-oxospiro (isobenzofuran-1(3H),9'-(9H)xanthene)-2,7-diyl)bis (methylene))bis(N-carboxymethyl)-acetoxymethyl ester), CFDA (C-195: 5-carboxyfluorescein diacetate) acridine orange (A-1301: 3,6-acridinediamine, N,N,N',N'-tetramethyl-monohydrochloride), calcein blue (H-1426: 7-hydroxy-4-methylcoumarin-8-methyleneiminodiacetic acid), Fura-2AM [F-1201: 5-oxazolecarboxylic acid 2-(6-(bis(2-((acetyloxy)methoxy)-2-oxoethyl)amino)-5-(2-(2(bis (2-((acetyloxy)methoxy)-2-oxoethyl)amino)-5-methylphenoxy)ethoxy)-2-benxofuranyl)-,(acetyloxy) methyl ester, fluorescein diacetate (F-1303) or carboxy calcein blue AM (C-1431: 7-hydroxy-4-carboxymethylcoumarin-8-methyleneiminodiacetic acid acetoxymethyl ester) and the like. Such dyes are well known in the art and are commercially available (Molecular Probes, Eugene Oreg.). Particularly preferred are the dyes BCECF-AM or calcein-AM. The numerals in the parenthesis indicates the product number for the listed fluorescent dyes that are available from Molecular Probes.

In one embodiment, the incorporation or uptake of fluorescent dyes specific for viable cells depends upon metabolic activity of the viable cell. In accordance with this embodiment, non-fluorescing dyes are taken up by viable cells and converted to a fluorescing product by an intracellular enzyme such as an esterase. The presence of intracellular fluorescence thereby indicates viability.

The various types of tissues to which the present invention is applicable include normal tissues as well as primary or metastatic tumors, including solid tumors (both carcinomas and sarcomas) and the like.

The various types of carcinomas (adeno, squamous and undifferentiated variants for carcinomas of various sites), to which the present assay are applicable include, for example, adrenal, bladder, breast, colon, kidney, lung, ovary, pancreas, prostate, thyroid, upper airways (head and neck), uterus (corpus and cervix), bile ducts, choriocarcinoma, esophagus, liver, parathyroid, rectum, salivary glands, small bowel, stomach, testis, tongue and urethra. The various types of sarcomas and other neoplasms to which the present assay are applicable include, for example, diffuse lymphomas, Ewing's tumor, Hodgkin's disease, melanoma (melanotic and amelanotic), multiple myeloma, nephroblastoma (Wilm's tumor), neuroblastomas, nodular lymphomas, rhabdomyosarcoma, angiosarcoma, brain tumors (gliomas), chondrosarcoma, dysgerminoma, fibrosarcoma, leiomyosarcoma, liposarcoma, medulloblastoma, mesothelioma, osteosarcoma, retinoblastoma and thymoma.

Typically, the tissue whose cell viability and/or proliferation characteristics are to be determined is explanted by an aseptic Surgical procedure and a portion thereof is divided into sections having a volume of about 0.5 to about 10, preferably a volume of about 1.0 to about 8.0, more preferably 1.0 to 2.0 cubic millimeters.

When tumors are being assayed, it is important to examine multiple portions of the tumor in separate assays because tumors are very heterogeneous.

After cubing, the explanted tissue is divided into aliquots (portions), typically at least about six, one of which is typically designated a control that receives no exposure or contact with the compound being examined. The aliquots are then histocultured on hydrated extracellular-matrix-containing gel so that the three-dimensional integrity of the tissue is maintained.

Drug exposure of the cells for the purposes of the viability and/or proliferation measurements is preferably carried out prior to treating the tissue samples with the viability and proliferation markers. The procedure involves incubating the tissue sample with a predetermined amount (determinate concentration) of the drug for a predetermined period of time (determinate time period) and thereafter separating the tissue sample from the drug, and preferably washing the tissue sample free of residual drug.

The phrase "drug exposure dose level", as used herein, refers to the quantitative product of the drug concentration (e.g. in µl) and the time of the exposure period (e.g., in hours or minutes). The drug concentrations and exposure times are typically calculated from pharmacological data to the simulate in vitro the drug exposure dose level achieved in vivo. Typically, it has been found that the drug exposure dose level required in carrying out the drug sensitivity measurements in accordance with the assay of the present invention, is at a maximum of only 5 to 10% of the clinically achievable drug exposure dose level for the known anticancer drugs which have been tested in the present system.

The drug sensitivity measurements as described above can be carried out in a manner which enables the determination, for any given drug, of a "drug sensitivity index", which is indicative of the antineoplastic activity of the given drug against the specific human tumor from which the explanted cells were obtained. This procedure involves carrying out the drug sensitivity measurements of a plurality of dose levels extending over a multi-log range, and then using the results of these measurements to plot a curve of percent survival (the percentage of the assay count resulting from drug exposure versus the assay count of the control in the absence of drug exposure) versus drug exposure dose level. The "drug sensitivity index" of the given drug is then quantitated by measuring the area under such curve out to a defined upper limit which is correlated to the clinically achievable peak drug exposure dose level for that drug.

The sensitivity index obtained in the above-described manner is highly indicative of the antineoplastic activity of the drug against the specific human tumor from which the explanted cells were obtained, with a low sensitivity index indicating high antineoplastic activity.

After histoculturing the cells in the presence of the agent being examined (about 1 to 4 days) the samples are treated (cultured in the presence of) the proliferation and/or viability marker.

After the cells of the tissue samples have been exposed to the drug(s), treated with the proliferation and viability markers and subsequently histocultured, the samples are typically fixed in the tissue fixative such as formalin, embedding in paraffin or the like and sectioned on a microtine. The sections are then assayed for the percentage of cells positive for the presence of the viability of proliferation marker and for calculating VCI and GFI as described herein.

When the viability and/or proliferation markers contain radioactive labels, the sections are then treated with nuclear-track emulsion such as NTB (Kodak), and developed. When radioactive labels and nuclear-track emulsions are used, this can be accomplished by light-polarized microscopy.

Where the markers are fluorescent dyes, the sections are stained with the appropriate dye(s), analyzed under fluorescence microscopy, and the numbers of dead and/or live cells are counted as described herein.

In preferred embodiments, the magnified image can be digitized by processing it through a video camera operatively linked to a computer capable of digitizing the image for analysis.

Preliminary evidence indicates that the in vitro assay system of the present invention has utility for the in vitro prediction of clinical response to cancer chemotherapy, as well as the screening of new anticancer drugs for clinical trial. For example, in treating a specific patient for a specific tumor, the explanted cells obtained from a biopsy of such specific tumor can be assayed in accordance with the present technique, whereby drug sensitivity measurements are made according to the present invention for a plurality of different anticancer drugs which are potentially clinically effective for the chemotherapeutic treatment of the specific tumor. After determining the relative drug sensitivity indices (e.g., GFI and/or VCI) for each of the various drugs tested, these sensitivity indices may be used for predictably selecting the most promising and/or effective of the drugs to be used for the chemotherapeutic treatment. In preliminary clinical trials of this technique, both retrospective and prospective, the correlation found between the in vitro prediction and the in vivo response for a particular agent by a particular tumor tissue type was improved dramatically where viability and proliferation were both evaluated.

In another embodiment, the present invention contemplates a kit for the in vitro determination of viability and/or proliferation of cells as described herein. The kit contains, in an amount sufficient for at least one assay, an agent to be tested for its effects on viability and/or proliferation, a viability and/or proliferation marker, and a container in which to perform the assay.

EXAMPLES

The following examples are given for illustrative purposes only and are not intended to be limiting unless otherwise specified.

1. Cell Proliferation in Histoculture

Various normal and tumor tissue specimens were ex-planted from human patients as described by Freeman et al., Proc. Natl. Acad. Sci. USA, 83: 2694–98 (1986); and by Vescio et al., Proc. Natl. Acad. Sci USA, 84: 5029–33 (1987). (The teachings of all of the references cited herein are hereby incorporated by reference). Briefly, after tissues were surgically removed, they were divided into 1- to 2-mm-diameter pieces and placed on top of previously hydrated extracellular-matrix-containing flexible gels derived from pigskin (Gelfoam, Upjohn) to form a three-dimensional culture. Eagle's minimal essential medium (MEM) containing Earle's salts, glutamine, 10% fetal calf serum, nonessential amino acids, and the antibiotics garamycin and claforan was added to the cultures such that the upper part of the gel was not covered, and cultures were maintained at 37 degrees C in a carbon dioxide incubator (95% sterile air/5% $CO_2$) to allow the explanted tissue specimens to grow.

Cells within the three-dimensional cultures capable of proliferation were labeled by administration of a combination of $^3$H-thymidine and $^3$H-deoxyuridine (2 μCi each; 1 Ci=37 GBq) (Vescio et al., Proc. Natl. Acad. Sci. USA, 84: 5029–33, 1987) for 4 days after 10–12 days in culture. Cellular DNA is labeled in any cells undergoing replication within the tissues. After 4 days of labeling, the cultures were washed with phosphate-buffered saline, placed in histology capsules, and fixed in 10% Formalin. The cultures were then dehydrated, embedded in paraffin, and sectioned by standard methods, and the sections were placed on slides.

The sections on the slides were then deparaffinized and prepared for autoradiography by coating with Kodak NTB-2 emulsion in the dark and exposed for 5 days, after which they were developed. After developing and rinsing, the sections were stained with hematoxylin and eosin.

The sections were then analyzed by determining the percentage of cells undergoing DNA synthesis in the various treated versus non-treated tumor tissue cultures, using a Nikon or Olympus photomicroscope fitted with an epi-illumination polarization lighting system. Replicating cells were identified by the presence of silver grains, visualized as bright green in the epi-illumination polarization system, over their nuclei due to exposure of the NTB-2 emulsion to radioactive DNA and subsequent green reflection of the polarized light by the silver grains. The above procedures produce a histological autoradiogram showing cellular proliferation of specific cells in the histocultured tumor explant tissue.

The large majority of tumors cultured in the native-state system demonstrate at least some areas of high cellular proliferation and are intratumorally heterogeneous with regard to proliferation capability. Tumors tested include tumors of the colon, ovaries, pancreas, bladder, kidney, brain, and parotid, and also include small-cell lung carcinoma and Ewing sarcoma. In all cases, three-dimensional tissue organization representative of the original tissue is maintained throughout the culture period. A high degree of detection of radiolabeled proliferating cells is afforded by the epi-illuminescence polarization microscopy, which enhances detection of the autoradiographic exposed silver grains by the scatter of incident polarized light.

The proliferation capacity of a metastatic colorectal tumor exhibited high labeling in culture. More than 90% of the cells in the observed culture preparation had proliferated during the labeling period of this relatively undifferentiated colon metastasis to the liver.

The proliferation capacity of a small-cell lung tumor exhibited the maintenance of the two major classes of oat cell types: the classic small cells and the more elongate fusiform cell types, each having a high degree of cell proliferation.

The proliferation capacity in ovarian carcinoma consistently exhibited an extremely high index of proliferation of the epithelial cells while the stromal cells remained quiescent. The histological autoradiogram showed the high proliferative capacity of the ovarian carcinoma cells which have invaded the supporting gel matrix. This invasive behavior may mimic the way ovarian tumors frequently invade the peritoneal wall in vivo.

The proliferation capacity in miscellaneous tumors, including those of the pancreas, bladder, kidney, brain, and parotid gland, and a Ewing sarcoma exhibited the intricate gland formations containing proliferating cells in many of these cultured tumors.

It is important to note that distinctions can be observed in the prepared autoradiograms between proliferating malignant cells and normal cell types, such as for the breast tumor epithelial cells and normal stromal cells.

An additional important observation in these studies is that normal tissues culture and proliferate well. Explanted tumor and adjacent normal tissue from the breast of patient 431 were compared. Extensive cell proliferations were noted to be present in the normal tissues. However, a higher level of tissue organization was observed to be maintained in the normal tissues. With this system if is now possible to compare tumor and normal biology—for example, nutritional requirements, growth factor requirements, and metabolic pathways. Also of critical importance, it is now possible to compare the antitumor selectivity of potential neoplastic agents by comparing tumor and normal response to drugs, using cell proliferation as an endpoint as described in Example 3.

These results have demonstrated a generalized system for measurement of proliferation capacity for all the major types of human tissues in relatively long-term culture. As mentioned above, all cultures described in this report have been viable in culture for 14 days, which is a relatively long period. Greater periods of culture can be achieved with most tissue specimens (data not shown). Greater than 90% of surgical specimens can be cultured and analyzed for proliferative capacity with this system.

This native-state culture system, with the aid of polarization microscopy, allows a high probability of detecting potential proliferative cells.

For image analysis of proliferating cells, a video camera was attached to the microscope. Autoradiograms prepared as above using breast carcinoma tissue were then viewed under polarizing light without bright-field light, thereby visualizing only the radioactive cells which have exposed silver grains of the nuclear-track emulsion. The radioactive cells brightly reflect the polarized light. The resulting image was analyzed by a computer-assisted image analysis apparatus in which the image was first digitized by a digitizer board, and then the area of brightness corresponding to the number of labeled or bright cells was calculated as the area of enhanced pixels by the Fas-Com version of the P-See program (The Microworks, Del Mar, Calif.) run on an IBM PC XT compatible computer. The area of enhanced pixels is proportional to the number of labeled cells.

With the image analysis system the autoradiograms were automatically analyzed for the number of labeled proliferating cells. With the bright-field and polarized light microscopy, the labeled cells of a cultured breast tumor appear bright green. With epi-illumination polarization microscopy using polarized light without bright-field, only the labeled cells were visualized. The image of the labeled cells was then digitized through a video camera and the P-See program. The area of brightness or enhanced pixels was then automatically determined by the Fas-Com program. The area of enhanced pixels is proportional to the number of labeled cells, enabling the automatic counting of labeled, proliferating cells.

An important aspect of the culture system is the use of a flexible extracellular-matrix-containing gel on which to ex-plant the tumors. Other investigators have noted that flexible extracellular-matrix-containing substrata are critical to growth and function of differentiated cells. Li et al., *Proc. Natl. Acad. Sci. USA*, 84: 136–40 (1987); Davis et al., *Science*, 236: 1106–9 (197); Schaefer et al., *Cancer Res.*, 43: 279–86 (1983); Schaefer et al., *Differentiation*, 25: 185–92 (1983); and Leighton, J., in *Tissue Culture Methods and Applications*, eds., Kruse et al., (Academic, New York), pp. 367–71 (1973).

The general principles here are applicable to all types of human tissues, allowing the accumulation of potential important biological and clinically prognostic information. In addition, it should be noted that many of these tumors have high capabilities of cell proliferation. The eventual understanding of the deregulation permissive for such proliferation should be facilitated with the system described here and allow us a deeper understanding of the changes occurring in oncogenesis.

2. Determining Cell Viability and Proliferative Capacity in Native-State Tissue Culture Tumor tissue specimens from a patient having breast carcinoma were obtained as described in Example 1, divided into 1 mm diameter pieces, and were each placed onto a flexible gel matrix to form a three dimensional culture. Duplicate cultures are prepared of each specimen, and 8 microcuries (µCi) of either $^{35}$S-methionine or $^{3}$H-thymidine was added to each culture that includes 2 milliliters (ml) of culture medium containing the added radiolabel. The labeled cultures were maintained as before for four days, the excess radiolabel was then rinsed off of each cultured specimen using a series of phosphate-buffered saline (PBS) rinses and the cultures were each processed for histological and autoradiographic visualization as described in Example 1.

The prepared cultures were then analyzed by using the computer program Fas-Com for analysis after digitizing as described in Example 1. The measure of $^{35}$-methionine incorporated into cultured cells allows the determination of cellular protein synthesis and is therefore a measure of cell viability. The measure of $^{3}$H-thymidine incorporation into cultured cells allows the determination of DNA synthesis and is therefore a measure of cell proliferation.

Tissue specimens cultured in the presence of $^{35}$S-methionine or $^{3}$H-thymidine incorporated radiolabel in the portions of the tissue containing viable or proliferating cells, respectively, or both. Non-viable or non-proliferating cells did not incorporate their respective labels and did not present silver grains on visual inspection of prepared specimens, nor present proliferating cells as bright green objects when analyzed in the epi-illumination polarization system.

The percentage of cells labelled with protein synthesis marker out of the total number of cells was determined in each culture. Similarly, percentage of cells labelled with the DNA-synthesis marker out of the total number of cells was determined in each culture.

The extent of proliferation measured by the in vitro native-state culturing system correlates with the grade and stage of the tumor: the more malignant the tumor, the higher the proliferation measured in vitro. The extent of proliferation can be expressed as a growth fraction index (GFI), measured as the percentage of proliferating cells present in a population of the total number of cells present in a selected field viewed by the microscope. Therefore measured GFI can be used to predict the clinical progression of the human cancer tissue tested. The Fas-Com program analysis provides a quantitative means that is semi-automated to determine the proliferative capacity or viability of a tumor, and is ideally suited to provide GFI data.

Proliferation and viability analyses were conducted on numerous explanted breast tumor tissues graded as metastatic or primary, and also graded as poorly or moderately differentiated to generate an average GFI for each type of tumor tested. Whereas metastatic tumors averaged 0.437±0.149 GFI, primary tumors exhibited a lower average of 0.282±0.138 GFI. Similarly, whereas poorly differentiated tumors averaged 0.372±0.150 GFI, moderately differentiated tumors averaged 0.220±0.094 GFI. The results indicate that GFI correlates with tumor severity and clinical prognosis.

3. Determining Drug Response Using The Native-State System For Measuring Viability And Proliferative Capacity Of Tissues In Vitro Tissue specimen cultures were established using various tumor tissues as described in Example 2. After the fourth day of culturing, multiple cultures of each tissue were further cultured in the presence of a drug as indicated below at the indicated concentrations for an exposure time of 24 hours.

Cultures were then washed in culture medium to remove excess drug, cultured in the absence of drug for 3 days to allow the cells to recover from transient drug effects, and were then labeled as described in Example 2. After labeling, the cultures were processed as before in Examples 1 and 2 to visualize the degree of viability and proliferative capacity in the specimens when cultured in the presence of the drug.

The cells cultured from the ovarian carcinoma tissue of a patient having ovarian carcinoma were tested by the above methods for cell proliferation in the presence of cisplatin at 1.5 µg/ml, 5-fluorouracil at 4 µg/ml, melphalan at 10 µg/ml, methotrexate at 22.5 µg/ml or thiotepa at 60 µg/ml. The results showed a decrease in the detectable signal generated by both $^{3}$H-thymidine and $^{35}$S-methionine incorporation, indicating an inhibition of both proliferation and viability. A diminution in cell proliferation is expressed as a decrease in the GFI, when compared in the GFI for the same specimen cultured in the absence of the drug. A diminution of cell proliferation was observed in an amount of 90% using cisplatin, 99% using 5-fluorouracil, 70% using melphalan, 70% using methotrexate and 90% using thiotepa. Patient S.D. having ovarian carcinoma produced explanted tumor tissue that was inhibited by more than 70% in cell proliferation by melphalan at 10 µg/ml, responded to therapy using melphalan, and exhibited a decrease in tumor size during treatments. Therefore a clinical correlation was demonstrated between in vivo responsiveness of the tumor to the drug and the in vitro native-state drug responsiveness.

The cells cultured from the tissue of a patient having breast carcinoma were tested as above in the presence of drug, and resulted in the following diminutions in cell proliferation shown in the parenthesis: Adriamycin at 290 ng/ml (90%), 5-fluorouracil at 4 µg/ml (90%), melphalan at 1 µg/ml (80%), methotrexate at 2.25 µg/ml (70%) or vincristine at 23 µg/ml (70%).

Patient D.H. was diagnosed as having breast carcinoma and was determined to be non-responsive to in vivo therapy with either 5-fluorouracil or adriamycin. Cellular proliferation of patient D.H.'s breast carcinoma tissue was not inhibited significantly (i.e. greater than 90% diminution) by culturing as above in the presence of either 5-fluorouracil or adriamycin. Therefore, there was a clinical correlation between in vivo responsiveness and in vitro diminutions of cell proliferation.

The cells cultured from the cancerous tissue from a patient (V.S.) colon/rectal cancer were tested as above in the presence of the various indicated drugs, and resulted in the following diminutions in cell proliferation shown in the parenthesis: 5-fluorouracil at 4 µg/ml (90%), mitomycin C at 1 µg/ml (90%), and BCNU at 2 µg/ml (90%). Patient V.S. was diagnosed as having colon carcinoma and was determined to be non-responsive to in vivo therapy using 5-fluorouracil. Cellular proliferation of V.S.'s colon carcinoma cells was not inhibited significantly, i.e., greater than 90%, by culturing the explants as above in the presence of 5-fluorouracil. A clinical correlation was again observed between in vivo and in vitro responsiveness.

The above results show that cellular proliferation can be used as a measure of a tumor's drug responsiveness, where an active drug inhibits cellular proliferation. Where cells are not in a proliferative state, the viability of the tumor tissue as measured by $^{35}$S-methionine incorporation can be used to indicate the tumor's drug responsiveness. The extent of viability can also be used to determine an endpoint for maximum responsiveness.

4. Fluorescent-Dye Endpoint Assay to Determine Chemosensitivity by Cell Viability A viability cell index (VCI) was also determined for histocultured tumor tissue by using fluorescent dyes to indicate the endpoint in a chemosensitivity assay. A first dye that is viable cell-specific and a second dye that is dead cell-specific are used to determine the VCI for the tumor tissue in the presence of a chemotherapeutic agent.

The viable cell-specific dye BCECF-AM, 2'7'-bis(2-carboxyethyl)-5(6)-carboxyfluorescein, is activated to fluorescence by non-specific esterases present only in living cells. The dead cell-specific dye PI, propidium iodide, enters only non-viable cells whose plasma membranes are leaky. Both dyes were added to the histoculture at 15 uM, and the cultures were analyzed by fluorescence confocal microscopy after 20 minutes of dye staining. Both dyes are used simultaneously on the same sample because the emission spectra of BCECF-AM and PI are different. The histocultured samples were observed using a MRC-600 Confocal Imaging System (Bio-Rad) mounted on a Nikon Optiphot fluorescent microscope fitted with a 10X PlanApo objective and a Nikon DN-510 B-2A fluorescence filter.

The fluorescence endpoint was determined using various drugs in a dose-response on histocultured human tumors for 24 hours. Samples were prepared for histoculture as described in Example 1. Thereafter, the viable cell index (VCI) was determined for both treated and control (untreated) histocultured samples.

5. $^3$H-Thymidine Endpoint Assay to Determine Chemosensitivity by Cell Proliferation Using the DNA-synthesis marker procedure described in Example 1, proliferation was measured in a series of human tumor histocultures following exposure to a variety of drugs as described in Example 4 and the proliferation index was calculated as a growth fraction index (GFI).

The samples were analyzed with confocal microscopy as described in Example 1 to count the number of proliferating cells in the histoculture. For each drug concentration tested, 1 to 3 microscope fields were observed and counted that contained the highest number of labeled cells in order to identify the areas in the heterogeneous tumor cultures having the least drug sensitivity. Control (untreated) cultures were evaluated and counted in the same manner. Six replicate cultures were evaluated for each drug concentration to determine a statistically significant in vitro drug response. An endpoint for in vitro drug responsiveness was the concentration at which a 50% reduction in GFI was observed when compared to control samples.

In a representative study, the GFI endpoint correlated well with a clinical study using cisplatin to treat patients having head and neck cancers. Patients with head or neck cancer were biopsied to produce a histoculture sample that was tested in the GFI endpoint assay as described in Example 1. Twenty-three patients who were treated with cisplatin were studied using the in vitro GFI assay, and ten out of twelve patients who tested as sensitive by GFI responded clinically (83%). In addition, seven out of eleven patients who tested as resistant by GFI demonstrated no clinical response (64%).

6. In Vivo Drug Response Assay

In order to assess the effectiveness of the present methods, in vivo drug dose-responsiveness was conducted and compared to the in vitro indexes generated by the present methods. To that end, the human tumors fragments of about 27 mm$^3$ described herein were inoculated under ether anesthesia by means of a trocar needle into the subcutaneous tissue on the back of a nude mouse.

All drugs were dissolved in 0.2 ml of physiological saline and administered at a schedule of q4dx3 i.p. except for doxorubicin, which was given i.v. Dosages administered were 3 mg/kg for mitomycin C, 4 mg/kg for doxorubicin, 50 mg/kg for 5-FU, and 80 mg/kg for cyclophosphamide, which were determined to be the maximum tolerable doses for nude mice when injected on the indicated schedule. Melphalan was used as the in vitro surrogate for cyclophosphamide which requires in vivo metabolic activation and cannot be tested readily in vitro.

After inoculation of the tumor tissue, and during administration of the drug, tumors were measured in the animal (length and width) with a sliding caliper three times weekly by the formula: tumor weight (W) in mg equals length (L) in mm times [width (W)]$^2$ divided by 2, or W=L×W$^2$/2. Typically, when tumors reached 100–300 mg, about 2–3 weeks after inoculation, tumor-bearing mice were randomized into test groups of six mice each. The relative mean tumor weight (RW) was calculated as Wi/Wo, where Wi is the mean tumor weight of a group at any given time (i) and Wo is the mean tumor weight at the initial treatment. Antitumor effect of the drug was expressed as a ratio of test to control RW, or Trw/Crw, when the ratio was at its lowest value during the treatment using Crw values obtained at the same time period as Trw. Antitumor activity was considered positive when the lowest Trw/Crw during the experiment was less than 42% of control reflecting a 25% reduction of the diameter of the tumor.

7. Comparison of Chemosensitivity Indexes

The chemosensitivity indexes GFI, determined as described in Example 5, and VCI, determined as described in Example 4, were obtained for a variety of histocultured human tumor tissue samples that were also tested for drug responsiveness in vivo as described in Example 6.

Using human small cell lung cancer (Lu24), it was determined that whereas doxorubicin produced a dose-response curve when assayed by both VCI or GFI, 5-FU exhibited relative resistance using VCI, even at high dosages of about 40 ug/ml (10X), where 1 X indicates the level of drug achievable in blood. Thus, different drugs differ in effectiveness against a particular tumor tissue when assayed in vitro.

Using human colon carcinoma (1863) it was determined that whereas 5-FU produces a dose-response of sensitivity by the tumor to 5-FU when assayed using the GFI assay, the tumor is not significantly responsive to 5-FU in the VCI assay. Thus, the GFI endpoint can lead to a false positive result when considered alone without the VCI endpoint data.

A panel of seven human tumors were similarly tested, including gastric cancers St-4 and St-40, colon cancer Co-4, breast cancer MX-1, and lung cancers Lu130, Lu24 and H69, which were all established as xenograft lines. These human tumors were evaluated for responsiveness to mitomycin C (MitC), doxorubicin (Dox), 5-fluorouracil (5-FU), cisplatin (Cis), and melphalan (Mel) using the in vivo assay, and the in vitro assays determining GFI and VCI. Overall, there was a reasonable degree of correlation between in vivo sensitivity and the drug responsiveness according to either VCI or GFI assays. For example, averaged over all tumor types (7 types) and all drugs (5 drugs), VCI was accurate 73% of the time and GFI was accurate 63% of the time, when compared to the in vivo result.

Notably, however, depending upon the tumor and the drug tested, a VCI end point and a GFI end point were occasionally observed to give opposite results regarding drug sensitivity. For example, in some cases VCI gave a false positive result whereas GFI gave a true negative result (i.e., the tissue was resistant to the drug when administered in vivo). Other combinations of opposing drug responsiveness results were also observed. For example, resistance with VCI and sensitivity with GFI to drug responsiveness was observed in 39.3% of the cases studied, whereas the reverse of an indication of sensitivity with VCI and resistance with GFI was observed in only 8.4% of the cases.

Based on the data, it is seen that the combination of both GFI and VCI substantially increases the reliability of the in vitro assay for predicting in vivo effectiveness of a particular drug against a particular tumor type by reducing the incidence of false positive results (i.e., incorrect indication of drug sensitivity). For example, it was observed that 55% of the false readings produced using a VCI assay were identified as results contradictory with in vivo data by the GFI endpoint assay, and 75% of the false readings produced using a GFI assay were identified as contradictory with in vivo data by the VCI endpoint assay. Therefore it is seen that when the in vitro VCI end point assay is utilized (measuring cell viability) in conjunction with the in vitro GFI end point assay (measuring cell proliferation), the comparative data synergistically lowers the false-positive rate for drug responsiveness in the in vitro histoculture assay. Furthermore, where both the VCI and GFI in vitro indices are in agreement, in vivo drug-responsiveness testing is not generally required, or can be substantially minimized due to the high reliability correlation from the in vitro assays.

8. Viability Assay Using Tetrazolium Metabolism

In another embodiment, the enzymatic conversion of a tetrazolium salt into an optically detectable formazan crystal was used as a marker for viable cells.

To that end, human tumor specimens were established in histoculture as described in Example 1. A panel of drugs known to have varying effectiveness against various types of cancer were exposed to the histocultured tumor tissues. Drugs used were mitomycin-C (about 100 ng/ml), doxorubicin (about 29 ng/ml), 5-fluorouracil (about 4 µg/ml), carmustine (about 0.2 µg/ml), cisplatin (about 1.5 µg/ml), melphalan (about 1 µg/ml), vinblastine (about 7.3 ng/ml), vincristine (about 23 ng/ml) and bleomycin (about 210 ng/ml), all from Sigma Chemical Co., (St. Louis, Mo.). The concentrations of these drugs represent approximately the levels achievable clinically and are termed "IX" concentrations. All were dissolved in physiological saline except for melphalan, which was dissolved in ethanol.

A phosphate-buffered saline solution composed of about 138.7 mM NaCl, about 2.7 mM KCl, about 8 mM $Na_2HPO_4$, about 1.5 mM $KH_2PO_4$ was prepared. A quantity of 3-(4,5-Dimethyl-2-thiazoyl)-2,5-diphenyl-2H-tetrazolium bromide (MTT) was dissolved in the phosphate-buffered saline to form a freshly prepared stock solution having about 8 mg/ml MTT. The solution was filtered through a 0.2-µm membrane filter from Millipore, (Bedford, Mass.).

The sponge-gel-supported tumor pieces, after about 24 hour incubation with the drugs, were transferred to drug free media and were incubated for about 2 hours at about 37° C. in a humidified sterile atmosphere, containing about 95% air and about 5% carbon dioxide with about 2 ml of a new solution composed of the MTT in the saline solution at a final concentration of about 0.4 mg/ml.

After about 2 hours, the gels were removed from the incubation media containing MTT and placed in about 2 ml of cold phosphate-buffered saline. The specimens were kept at about 4° C., and subsequently frozen whereupon 4-µm frozen sections were made. Water-soluble embedding media Tissue Tek OCT Compound from Baxter Labs (Irvine, Calif.) and a Tissue Tek II Cryostat, from Miles Laboratories, Inc. (Naperville, Ill.) were used in making the frozen sections.

The slides were then dipped for about 30 s in an about 1.25 µg/ml propidium iodide solution from Sigma, prepared in distilled water. After being dried, they were ready for pixel image analysis of formazan crystals (PIAFC) and pixel image analysis of fluorescent dye (PIAFD) measurements as described herein.

The image analysis system consisted of a Nikon Optiphot microscope connected to an RCA TC-1501 video camera, a Hitachi monitor and an IBM personal computer.

The measurements were conducted microscopically under a mercury lamp, using an IGS filter for polarized light and a DM 580 G-2A filter, composed of EX 510-560 excitation and BA 590 emission filters, for fluorescent light of the proper wavelength. The objective magnification was 200 X and the image was digitized by a conventional digitizer board.

The areas of brightness corresponding to the amount of formazan crystals which reflect polarized light or to red nuclei due to fluorescence of the propidium iodide fluorescent dye were calculated as the ratio of the area of enhanced pixels to total pixels by the Image Scanner, Conway Filter and Bright Pixel Planimeter (DS-88 Digisector Video, Confil version 1.0 program from The Microworks, Del Mar, Calif.) running on an IBM PC-XT type computer.

The PIAFC and the PIAFD were measured in the non-drug-treated control twice, once at the beginning of the experiment and once at the end, within about 6 hours of the beginning. During this time there were no statistically significant changes detected, indicating that the system was stable during the measurement period.

The analysis of a frozen section of the colon tumor under polarized light after about 24 h culture in the presence of doxorubicin and about 1 h incubation with MTT showed formazan crystals that were easily observed. The same field visualized under fluorescent light after staining with propidium iodide illustrated that areas of high formazan crystal formation correspond to areas that contain nuclei. The absence of nuclei in some areas of the section corresponds to the absence of formazan crystals in those areas, thus demonstrating that MTT is being reduced only by cells and not by the drug used with this histocultured tissue sample. The data shows that the tumor is not significantly sensitive in vitro to the drug doxorubicin (at 29 ng/ml) after the 24 h exposure.

A different frozen section of the same tumor incubated for about 24 h with a different drug, 1.5 µm/ml cisplatin, illustrated that the PIAFC is very low with respect to PIAFD, so that their ratio divided by the control value (using the formula described above) is only 0.25%. Using that formula, the tumor is calculated to be 99.75% sensitive in vitro to the drug cisplatin.

These data indicate that tetrazolium salts can be used as a metabolic marker to detect cell viability in in vitro histoculture assays for measuring chemosensitivity of tumor tissues to antineoplastic drugs.

The foregoing description and the examples are intended as illustrative and are not to be taken as limiting. Still other variations within the spirit and scope of this invention are possible and will readily present themselves to those skilled in the art.

What is claimed is:

1. An in vitro method for predicting the effectiveness of treating a preselected tumor tissue of a subject in vivo with an anti-tumor agent, which method comprises:
    a) histoculturing, in separate containers, first, second, third and fourth portions of a tumor tissue sample;
    b) exposing said first and second portions of said tumor tissue sample to said agent;
    c) determining the percentage of viable cells within said first and third portions of said histocultured tumor tissue sample to produce a viable cell index comprising a ratio of viable to non-viable cells in said first and third portions;
    d) determining the percentage of proliferating cells within said second and fourth portions of said histocultured tumor tissue sample to produce a growth fraction index comprising a ratio of proliferating to non-proliferating cells in said second and fourth portions; and
    e) wherein a reduced viable cell index in said first portion as compared to said third portion combined with a reduced growth fraction index in said second portion as compared to said fourth portion substantially increases the reliability of the in vitro as say as predicting in vivo effectiveness of said antitumor agent against said tumor tissue.

2. The method of claim 1 wherein the percentage of viable cells is determined by a process which comprises measuring the number of cells in said histocultured tissue sample that incorporate a protein synthesis marker.

3. The method of claim 2 wherein said protein synthesis marker is $^{35}$S-methionine.

4. The method of claim 1 wherein the percentage of viable cells is determined by a process which comprises measuring the number of cells in said histocultured tissue sample that incorporate a viable cell specific dye.

5. The method of claim 4 wherein said viable cell specific dye is selected from the group consisting of 2'7'-bis-(2-carboxyethyl)-5-(and-6)-carboxyfluorescein acetoxymethyl ester (BCECF-AM); glycine-N,N'-((3',6'-dihydroxy-3-oxospiro(isobenzofuran-I(3H),9'-(9H)xanthene)-2,7-diyl) bis(methylene))bis(N-carboxymethyl)-acetoxymethyl ester (calcein-AM); 5-carboxyfluorescein diacetate (CFDA); 3,6-acridinediamine, N,N,N',N'-tetramethyl-monohydrochloride (acridine orange); 7-hydroxy-4-methylcoumarin-8-methyleneiminodiacetic acid (calcein blue); 5-oxazolecarboxylic acid 2-(6-(bis(2-((acetyloxy)methoxy) -2-oxoethyl)amino)-5-(2-(2(bis(2-((acetyloxy)methoxy)-2-oxoethyl)amino)-5-methylphenoxy)ethoxy)-2-benxofuranyl)-(acetyloxy)methyl ester (fura-2AM), fluorescein diacetate and 7-hydroxy-4-carboxymethylcoumarin-8-methyleneiminodiacetic acid acetoxymethyl ester (carboxy calcein blue-AM).

6. The method of claim 2 wherein said process further comprises measuring the number of cells in said histocultured tissue sample that incorporate a dead-cell specific dye.

7. The method of claim 6 wherein said dead-cell specific dye is selected from the group consisting of propidium iodide, ethidium bromide and ethidium homodimer.

8. The method of claim 1 wherein the percentage of viable cells is determined by a process which comprises measuring the number of cells in said histocultured tissue sample that metabolically convert a detectable marker.

9. The method of claim 8 wherein said detectable marker that is metabolically converted by said viable cells is a tetrazolium salt.

10. The method of claim 9 wherein said tetrazolium salt is 3-[4,5-dimethylthiazol-2-yl]-2,5-diphenyltetrazolium bromide (MTT).

11. The method of claim 1 wherein the percentage of proliferating cells is determined by a process which comprises measuring the number of cells in said histocultured tissue sample that incorporate a DNA-synthesis marker.

12. The method of claim 11 wherein said DNA-synthesis marker is selected from the group consisting of $^{3}$H-thymidine, $^{3}$H-deoxyadenosine, $^{3}$H-deoxyguanosine, $^{3}$H-deoxycytidine and $^{3}$H-deoxyuridine.

13. The method of claim 1 wherein the percentage of viable cells is determined by a process which comprises measuring the number of cells in said histocultured tissue sample that incorporate a fluorescent dye indicative of viability and the percentage of proliferating cells is determined by a process which comprises measuring the number of cells in said histocultured tissue sample that incorporate the DNA-synthesis marker $^{3}$H-thymidine.

14. A kit for in vitro prediction of the effectiveness of in vivo treatment of a tumor with an anti-minor agent, which kit comprises a viable cell-specific marker for measuring cell viability in vitro and a cell proliferation marker for measuring cell proliferation in vitro, said markers each present in an mount sufficient to perform at least one in vitro determination.

15. The kit of claim 14 wherein said viable cell-specific marker is the fluorescent dye 2'7'-bis-(2-carboxyethyl)-5-(and-6)-carboxyfluorescein acetoxymethyl ester (BCECF-AM) and said cell proliferation marker is $^{3}$H-thymidine.

16. An in vitro method for predicting the effectiveness of treating a preselected tumor tissue of a subject in vivo with an antitumor agent which method comprises determining the viability of tumor cells in a histocultured sample of said tumor in the presence and absence of said agent;

determining the proliferation of tumor cells in a histocultured sample of said tumor tissue in the presence and absence of said agent;

wherein a reduction of viability of said cells in the presence as compared to the absence of said agent combined with a reduction in proliferation of said cells in the presence as compared to the absence of said agent substantially increases the reliability of the in vitro as predicting in vivo effectiveness of said antitumor agent against said tumor tissue.

* * * * *